Figure 1:
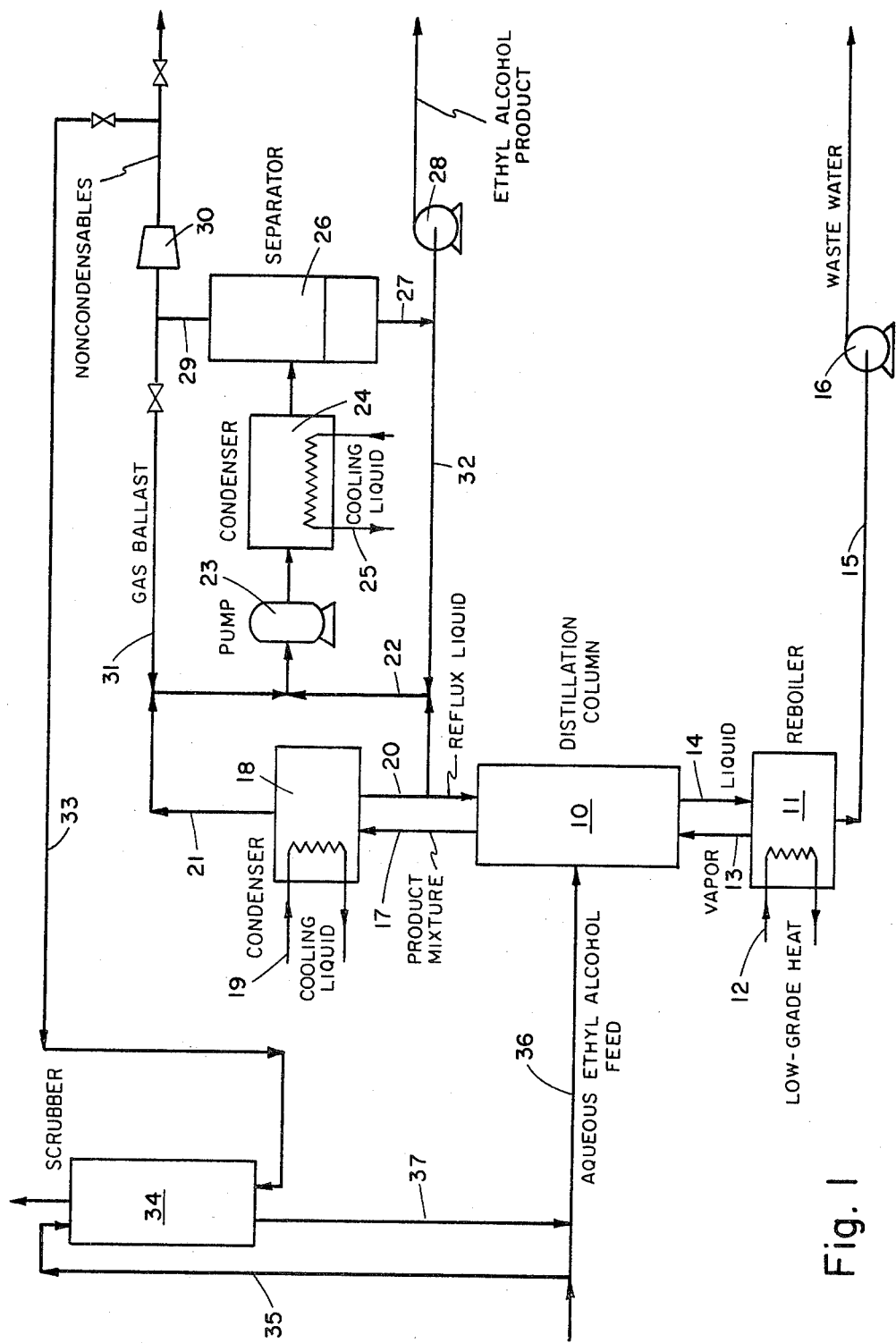

United States Patent [19]

Field

[11] 4,303,478
[45] Dec. 1, 1981

[54] PROCESS FOR DISTILLATIVELY SEPARATING LIQUID MIXTURES

[75] Inventor: Edwin L. Field, Lexington, Mass.

[73] Assignee: Arthur D. Little, Inc., Cambridge, Mass.

[21] Appl. No.: 182,116

[22] Filed: Aug. 28, 1980

[51] Int. Cl.$^3$ .......................................... B01D 3/16
[52] U.S. Cl. ..................................... 203/19; 203/24; 203/26
[58] Field of Search ...................... 203/19, 24, 26, 42, 203/49, DIG. 5

[56] References Cited

U.S. PATENT DOCUMENTS

| | | | |
|---|---|---|---|
| 2,327,643 | 8/1943 | Houghland | 203/26 |
| 2,509,136 | 5/1950 | Cornell | 203/26 |
| 2,992,978 | 7/1961 | Kelly | 202/186 |
| 3,230,155 | 1/1966 | Schürch | 203/26 |

Primary Examiner—Frank Sever
Attorney, Agent, or Firm—Richard J. Hammond

[57] ABSTRACT

Process for distillatively separating a liquid mixture containing at least two miscible volatile components having different boiling points using low-grade heat and, if necessary, low-grade cooling. Distillation is carried out at a pressure sufficiently low to cause the mixture at the bottom of the distillation column to boil below the temperature of the low-grade heat supplied and condensation of at least a portion of the vapor fraction is carried out at a pressure which permits using available cooling liquid. Condensed liquid is returned as reflux to the distillation column at a temperature and pressure essentially equal to the temperature and pressure prevailing near the top of the column. The progressive increase of vapor recompression in the system makes it possible to provide an increasing proportion of the energy to the system in the form of electrical energy, up to the total energy requirement. The process and apparatus of this invention are particularly suited to separating ethyl alcohol from dilute aqueous mixtures, where the formation of the ethyl alcohol azeotrope can be reduced or eliminated.

18 Claims, 4 Drawing Figures

PROCESS FOR DISTILLATIVELY SEPARATING LIQUID MIXTURES

This invention relates to process and apparatus for distillative separation of liquid mixtures and more particularly to process and apparatus for separating such mixtures using low-grade heat to effect vacuum distillation of the lower-boiling liquid in almost pure form.

In the commercial processes used for manufacturing many of the volatile water-soluble liquid organic compounds, it is often necessary to separate such organic compounds from aqueous solutions. In many of these mixtures water constitutes a major portion of the solution; and in a large number of these cases the water and organic liquids form azeotropes. The separation of many of these organic compounds from water requires relatively large and complex distillation equipment and demands a heavy expenditure of energy. Likewise, petroleum fuel fractions and light hydrocarbons must be separated from other organics such as higher boiling hydrocarbons with which they are miscible. The production of large quantities of ethanol may be used as an example of the process and apparatus with which the invention is concerned.

With the recent shifting from petroleum-derived fuel to other forms of energy, the use of alcohols, particularly ethanol, has received a great deal of attention. Ethanol can be readily formed through the fermentation of sugars derived from such agricultural products as sugar cane, bagasse, corn, molasses and the like, thus eliminating the need for petroleum cuts in its synthesis. However, the final product of such fermentation is a dilute solution of alcohol (typically about six percent by weight) in an aqueous solvent which also contains such noncondensables as carbon dioxide and air. Since a large part of the energy used in alcohol synthesis from agricultural materials is consumed in the distillation of the alcohol from the dilute aqueous mixtures, it is desirable to decrease the fuel required for such distillation. By using waste heat, the process and apparatus of this invention make possible this desired result.

It is, therefore, a primary object of this invention to provide an improved process for the distillative separation of liquid mixtures, the improvement residing primarily in a marked reduction in the fuel required to effect such separation by utilizing relatively low-grade waste heat as well as low-grade cooling liquids. It is another object of this invention to provide a process of the character described which makes it possible in some systems to avoid the formation of any appreciable quantities of azeotropes. A further object of this invention is to provide an improved process for separating and recovering ethanol from agricultural materials in a manner to achieve a net energy gain. Still another object is to provide such a process which is flexible in its use of various sources of energy, up to and including the exclusive use of electrical energy, and in its use of cooling liquid available over a relatively wide temperature range.

Another principal object of this invention is to provide improved apparatus for the distillative separation of liquid mixtures normally forming azeotropes. A further object is to provide apparatus of the character described which is particularly suited to the use of a low-grade heat source and which provides flexibility with regard to the type and source of such heat as well as to the type and source of cooling liquid. Still another object of this invention is to provide apparatus for the separation and recovery of ethanol in essentially pure form from agricultural materials.

Other objects of the invention will in part be obvious and will in part be apparent hereinafter.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

Figure 2:
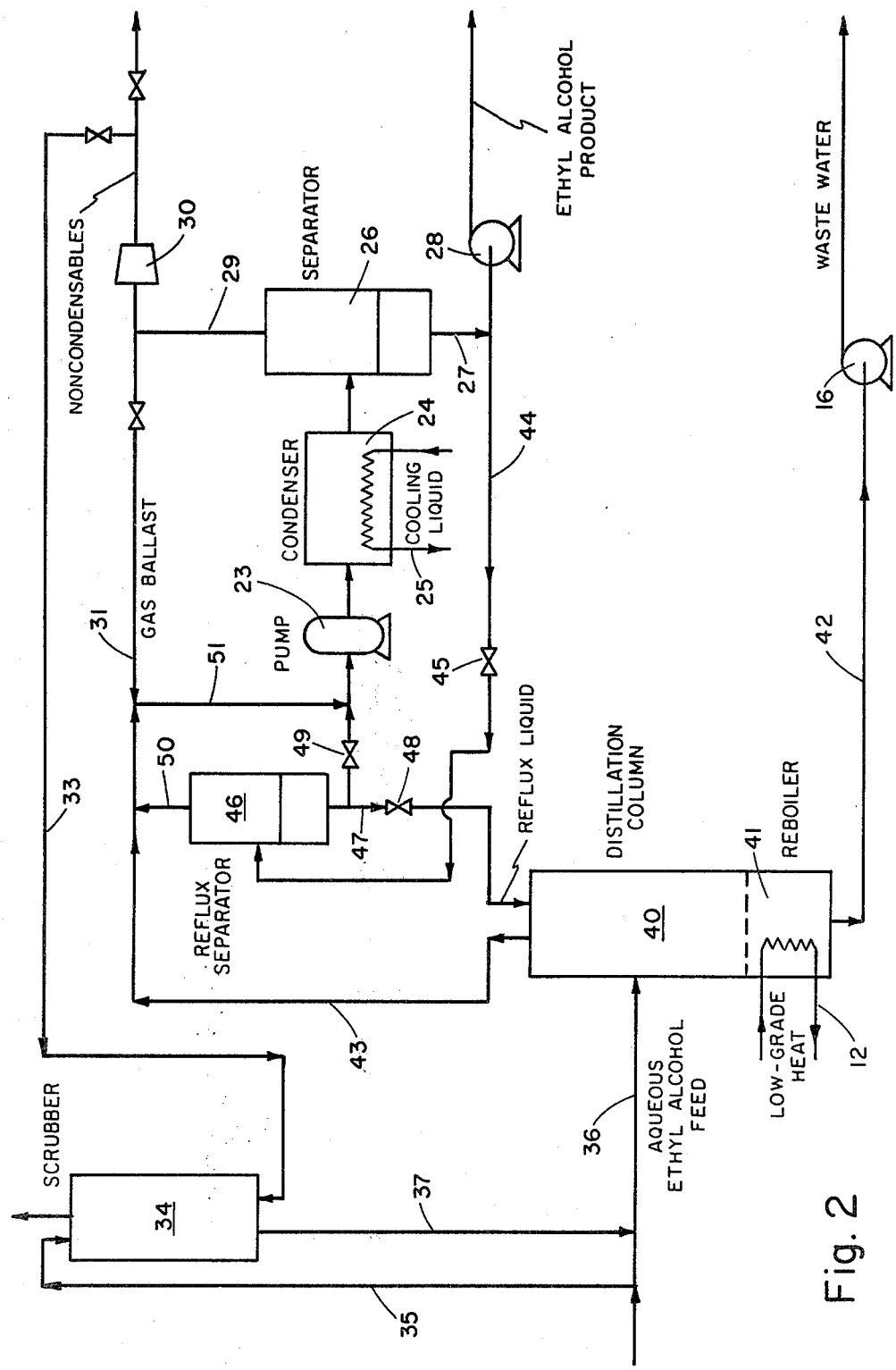
Figure 3:
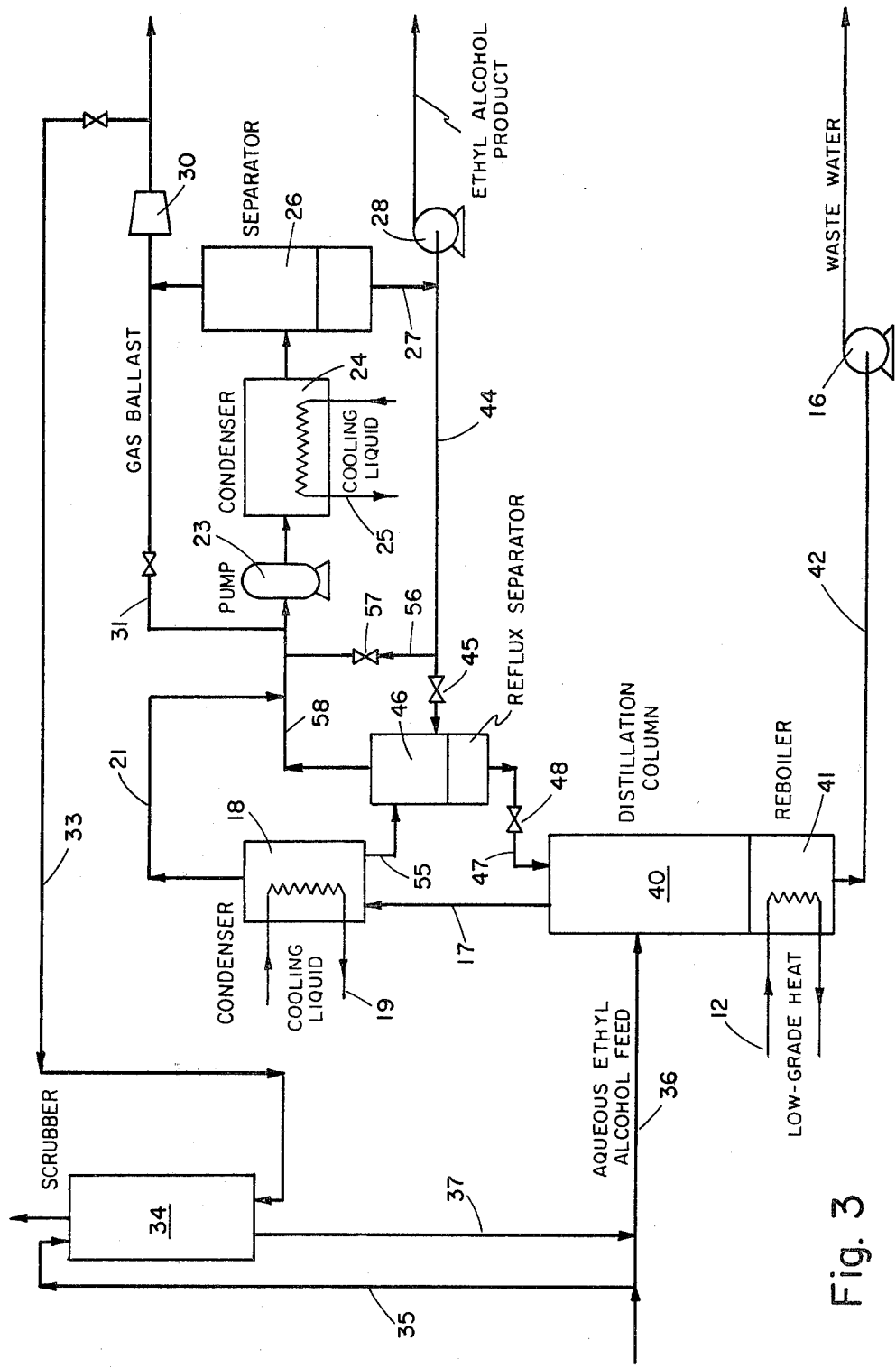
Figure 4:
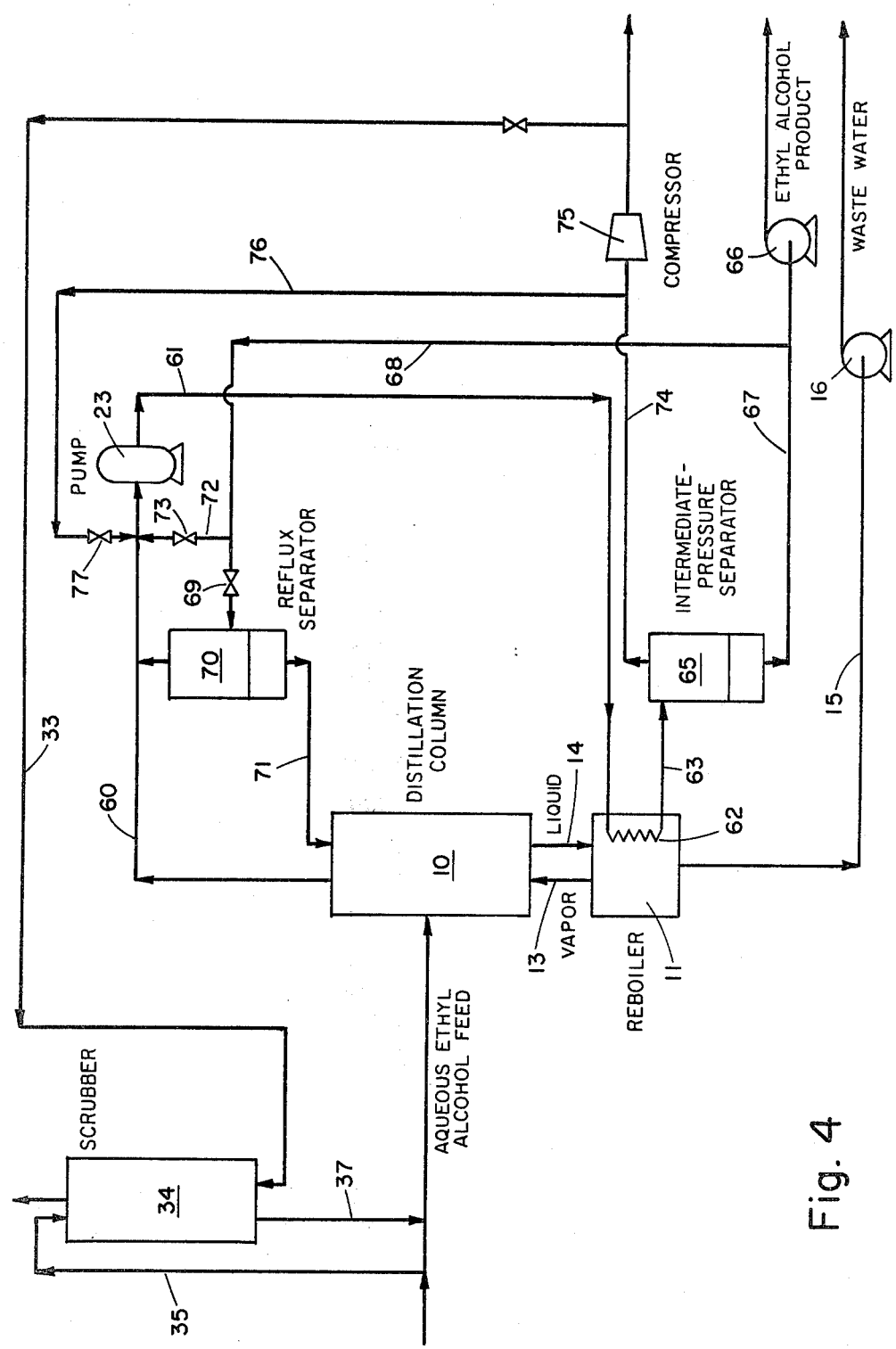

For a fuller understanding of the nature and objects of this invention, reference should be had to the following detailed description taken in connection with the accompanying drawings in which FIG. 1 illustrates one embodiment of the apparatus of this invention particularly suited to those situations wherein waste heat at a temperature of 40° C. or above and cooling water at between about 15° C. and about 30° C. are available;

FIG. 2 illustrates another embodiment of the apparatus suited to those situations wherein waste heat at between about 30° C. and 40° C. and cooling water at between about 20° C. and 30° C. are available;

FIG. 3 illustrates a modification of the apparatus embodiments of FIGS. 1 and 2 which, in effect, combines features of each embodiment; and FIG. 4 illustrates yet another embodiment of the apparatus of this invention incorporating additional vapor recompression means to eliminate the need for supplying both the waste heat and cooling liquid from external sources.

According to one aspect of this invention there is provided a process for distillatively separating liquid mixtures containing at least two miscible volatile components having different boiling points, comprising the steps of supplying to a distillation column a source of low-grade heat between about 30° C. and about 80° C.; supplying a cooling liquid; distilling a liquid mixture of at least two miscible volatile components of different boiling points in a distillation column, to form a lower-boiling fraction and a higher-boiling fraction, under a pressure sufficiently below atmospheric to cause the higher-boiling fraction of the liquid mixture to boil below the temperature of the low-grade heat supplied to the distillation column; discharging the higher-boiling fraction from the bottom of the distillation column; withdrawing from the distillation column the lower-boiling fraction at a pressure essentially equivalent to that prevailing near the top of the distillation column; elevating the presssure of the lower-boiling fraction to a level which is no greater than that which effects the condensing of at least a portion of the lower-boiling fraction above the temperature of the cooling liquid supplied to form lower-boiling liquid product; condensing a portion of the lower boiling fraction to provide the lower-boiling fraction at a low temperature and at a pressure essentially equal to that prevailing near the top of the distillation column; and returnig at least a portion of the low-temperature lower-boiling fraction to the top of the distillation column as reflux liquid.

According to another aspect of this invention there is provided a process for recovering ethyl alcohol from a dilute aqueous mixture containing noncondensable components, comprising the steps of supplying to a distillation column a source of lowgrade heat between about 30° C. and about 80° C.; supplying a cooling liquid; distilling a dilute aqueous mixture of ethyl alcohol and noncondensables in the distillation column, to form an ethyl alcohol product mixture and an aqueous waste mixture, under a pressure sufficiently below atmospheric to cause the aqueous waste mixture to boil below the temperature of the low-grade heat supplied to the distillation column; discharging the aqueous waste mixture from the bottom of the distillation column; withdrawing from the distillation column the ethyl alcohol product mixture containing the noncondensables at a pressure essentially equivalent to that prevailing near the top of the distillation column; elevating the pressure of the withdrawn ethyl alcohol product mixture to a level which is no greater than that which effects the condensing of the ethyl alcohol above the temperature of the cooling liquid supplied, to form ethyl alcohol product and gaseous noncondensables; separating the liquid ethyl alcohol product and the noncondensables; throttling a portion of the ethyl alcohol product mixture to provide a low-temperature liquid ethyl alcohol at a pressure essentially equal to that prevailing near the top of the distillation column; and returning at least a portion of the low-temperature liquid ethyl alcohol to the top of said distillation column as reflux liquid.

According to another aspect of this invention there is provided apparatus for distillatively separating a liquid mixture containing at least two miscible volatile components having different boiling points, comprising, in combination distillation column means capable of operating at subatmospheric pressures down to about 30 torr to produce a lower-boiling fraction product and a higher-boiling fraction; means to deliver to the distillation column a feed liquid of a mixture of at least two miscible liquid fractions having different boiling points; reboiler means associated with the distillation column means arranged to collect the higher-boiling fraction; means to supply low-grade heat to the reboiler means through indirect heat exchange with the higherboiling fraction; pump means to withdraw the higher-boiling fraction, from the reboiler at atmospheric pressure; cooling means operable at a pressure essentially equivalent to that prevailing near the top of the column means to effect condensation of at least a portion of the lower-boiling fraction product for reflux liquid in the distillation column means; condenser means including means to circulate a cooling liquid therethrough for indirect heat exchange with fluid therein; pump means capable of pumping the lower-boiling fraction product as a fluid mixture of liquid and condensing vapor from the distillation column into the condenser means at a pressure no greater than that which effects the condensing of the fluid mixture above the temperature of the cooling liquid circulating through the condenser means to provide the lower-boiling fraction as a liquid product; separator means for separating lower-boiling liquid product from any noncondensable gases; and pumping means for delivering the lower-boiling liquid product at atmospheric pressure.

In the following detailed description of this invention, it will be convenient to use as exemplary the separation of a dilute aqueous ethyl alcohol solution, containing such non-condensables as carbon dioxide and air, into an essentially pure ethyl alcohol and aqueous waste containing a very minor amount (e.g., up to about 0.05% by weight) of the alcohol. As will be apparent, the process and apparatus of this invention are particularly suited to the recovery of alcohol from the aqueous liquid resulting from the fermentation of agricultural materials and containing about 6% by weight ethyl alcohol.

FIG. 1 illustrates one embodiment of the apparatus of this invention particularly suitable for situations wherein low-grade heat at about 40° C. or above is available for heating the liquid feed mixture and a cooling liquid, e.g., water, is available at a temperature of between about 15° C. and about 30° C. In the apparatus of FIG. 1 there is provided distillation column means 10 having a reboiler 11 which may, of course, be incorporated into the bottom of distillation column 10. Distillation column 10 must be designed to be operated over a pressure range which includes pressures sufficiently below atmospheric to cause the aqueous waste mixture to boil below the temperature of the heat source. Distillation column 10 must contain an efficient packing capable of achieving good contact between the vapor and liquid phases. Moreover, the packing should preferably result in a relatively low pressure drop throughout the length of the column, the pressure drop preferably being no more than that required to provide the desired driving force within the column. Exemplary of a suitable packing is that sold as Koch-Sulzer packing and is characterized by its low pressure drop per theoretical plate height.

In the distillative separation of ethyl alcohol from a dilute aqueous mixture, the pressure at the bottom of column 10, as well as in reboiler 11, preferably ranges between about 40 and about 100 torr which means that the low-grade heat, supplied in the form of a heat exchange liquid through coils 12, must range in temperature from about 35° C. to about 45° C. That is, the temperature of this source of heat must be above the boiling point of the aqueous waste at the pressure in the bottom of the column. This temperature requirement is well within the range of many sources of so-called waste heat, e.g., condensate or low-grade steam from boilers; waste water from indirect heat exchangers used in various processes, and the like. In the embodiment of FIG. 1, reboiler 11 is shown as a separate apparatus component in fluid communication with distillation column 10 through vapor line 13 and liquid line 14. As noted above, reboiler 11 may, alternatively, be an integral part of distillation column 10. The aqueous waste mixture formed in the distillation of the feed liquid and containing any insolubles is withdrawn from reboiler 11 through line 15 and is pumped up to atmospheric pressure in pump 16 for discharging.

The pressure at the top of distillation column 10 preferably ranges between about 30 and 70 torr. The ethyl alcohol product mixture containing noncondensables is withdrawn from column 10 and is taken by line 17 into condenser 18 which is maintained at essentially the same reduced pressure as prevails at the top of column 10. Cooling liquid is circulated through coils 19 to effect indirect heat exchange with the product mixture and to condense a portion of the ethyl alcohol, the amount condensed being at least that quantity required to be returned as reflux liquid to column 10 through line 20. In the embodiment of FIG. 1 wherein the step of condensing a portion of the ethyl alcohol product mixture is effected in condenser 18, it is necessary to provide a cooling liquid at a temperature below the condensation temperature of ethyl alcohol at the reduced pressure prevailing in condenser 18. Thus where this pressure ranges between about 30 and about 70 torr, the cooling liquid must range between about 10° C. and 25° C. There are, of course, a number of sources of water within this temperature range for use as a cooling liquid, for example, ground water and water from streams or lakes in the temperate climates.

The ethyl alcohol product mixture which is not condensed in condenser 18, as well as any condensed ethyl alcohol mixture not required for refluxing, is pumped through lines 21 and 22, respectively, by pump 23 into a condenser 24. Pump 23 must be of the type capable of pumping a liquid containing condensing vapors. Exemplary of such a pump is the liquid ring vacuum pump, e.g., the well-known Nash pump.

Condenser 24 is maintained at a pressure which, in turn, is determined by the quality of the cooling liquid available for circulation through coils 25. Thus the pressure in condenser 24 is maintained at a level somewhat greater than that which will effect the condensing of the ethyl alcohol product somewhat above the temperature of the cooling liquid supplied. A suitable pressure for condenser 24 is readily determinable from existing data with respect to the vapor pressure of ethyl alcohol at various temperatures. For example, if it is desired to operate condenser 24 at atmospheric pressure, then the cooling liquid must be at a temperature below about 75° C., ethyl alcohol having a vapor pressure of 760 torr at 78.4° C.

If condenser 24 is operated at a pressure below atmospheric, then the ethyl alcohol product mixture must be pumped to atmospheric pressure by pump 28 upon its transference from separator 26 through line 27 to a use point or to a suitable storage reservoir (not shown). The noncondensables are withdrawn as gases from separator 26 through line 29 and compressor 30. Under some circumstances of operation it may be desirable to return a predeterminable quantity of the noncondensed gases into pump 23 and this may be done through gas ballast line 31 which communicates with line 21. Likewise, it may be desirable to recycle some of the ethyl alcohol from separator 26 into pump 23 by way of lines 32 and 22. It will be appreciated that any arrangement for recycling these materials may be used, that shown in FIG. 1 being only for illustration of one exemplary arrangement. Finally, as an optional step, a noncondensable purge from compressor 30 may be taken by line 33 through a scrubber 34 in which a stream 35 of incoming aqueous ethyl alcohol feed, diverted from the main feed line 36, is used to wash most of the residual alcohol from the purge prior to being returned to feed line 36 through return line 37.

The process and apparatus embodiment illustrated in FIG. 2, wherein the same reference numerals are used to identify the same components shown in FIG. 1, allow the use of a warmer cooling water for condensation and/or a cooler source of low-grade heat for the reboiler than it is possible to employ in the embodiment of FIG. 1. This is made possible through the use of heat pump means comprising the distillation column 40, the pump 23 serving as a compressor, the condenser 24 and throttle valve means.

In FIG. 2 the distillation column 40 is shown to have a reboiler 41 as an integral part thereof, thus requiring only liquid line 42 to remove waste water through pump 16. The ethyl alcohol product mixture is pumped out of column 40 through line 43 by pump 23 directly into condenser 24 wherein the pressure of the ethyl alcohol product mixture is elevated to a level which is no greater than that which will effect condensation of ethyl alcohol above the temperature of the cooling liquid circulated through coils 25. The practical maximum pressure usable in condenser 24 is atmospheric, making it possible to use cooling water as warm as about 70° C. to 75° C. However, with cooler cooling water, condenser 24 may more usually be operated at pressures below atmospheric, and this may be advantageous to minimize the size and energy requirement of pump 23. Again, as in the case of the embodiment of FIG. 2, separator 26 may be maintained at atmospheric pressure or below, using, if necessary pump 28 and compressor 30 to bring the product ethyl alcohol and noncondensables to atmospheric pressure.

In order to provide the required low-temperature ethyl alcohol as reflux liquid to distillation column 40, a portion of the ethyl alcohol product withdrawn from separator 26 is taken by way of line 44 and throttle valve 45 into a reflux separator 46, maintained at essentially the same pressure as that prevailing in the upper part of column 40. This results in flashing at least a portion of the ethyl alcohol in reflux separator 46 wherein the vaporization of a portion of the ethyl alcohol chills the remainder to provide the required reflux liquid which is returned through line 47, controlled by valve 48, to distillation column 40. The cold vapor from reflux separator 46 is directed through lines 50 and 51 into pump 23; and some of the cold liquid from reflux separator 46 is directed through valve 49 to pump 23 to maintain the liquid ring in the pump.

The embodiment illustrated in FIG. 3 is, in effect, a combination of the embodiments of FIGS. 1 and 2 in that both a condenser 18 and reflux evaporator 46, maintained at distillation column pressure, are used to provide ethyl alcohol condensate. The embodiment of FIG. 3 is suitable for those situations wherein some relatively cold (e.g., about 18° C. or colder) water or other liquid is available for at least part of the cooling of the ethyl alcohol product mixture. The availability of this quality of cooling liquid makes it possible to reduce the size of the liquid ring pump and hence to decrease its energy costs.

As will be seen in FIG. 3, in which the same reference numerals are used to identify the same components shown in FIGS. 1 and 2, condenser 18 is operated at essentially the same pressure as prevails at the top of column 40. If this column pressure is, for example, about 40 torr, then the cooling water, or other liquid, circulated through coils 19 must be at 18° C. or lower to achieve condensation of at least a portion of the liquid in the ethyl alcohol product mixture brought to condenser 18 through line 17. Some of the liquid from condenser 18 is taken by line 55 to reflux separator 46; while the noncondensed product and remaining liquid is pumped out through line 21. As in the case of the embodiment of FIG. 2, a portion of the product ethyl alcohol from separator 27 is sent by way of line 44 through throttle valve 45 into reflux separator 46 wherein a portion of the alcohol is vaporized and cooled for combining with the condensed liquid from condenser 18. The reflux liquid required in column 40 is withdrawn from reflux separator 46 and the balance of liquid and gas required for efficient operation of pump 23 is diverted from line 44 by way of line 56, having valve 57, and from evaporator 46 by way of line 58. Final condensation of the ethyl alcohol product is carried out in condenser 24 as previously described.

The embodiment of FIG. 3 limits the relative quantities of products which pump 23 must handle and therefore means that less pumping work must be supplied.

In the embodiment of FIG. 4, the low-grade heat and cooling liquid are supplied within the total system, making it unnecessary to supply either from an external source. This, in turn, means that the energy to operate the liquid ring pump makes up essentially the total energy requirement for the system, thus making it possible to limit the energy requirements to electrical energy alone.

As will be seen from FIG. 4, the ethyl alcohol product mixture withdrawn from distillation column 10 through line 60 is adiabatically compressed by pump 23 to that pressure level which will raise the condensing temperature of the product mixture to the necessary level so that it may be used as a source of low-grade heat. Therefore this heated, compressed fluid from pump 23 is taken through line 61 to coils 62 in reboiler 11, and the liquid in reboiler 11 serves as the required cooling liquid to effect condensation of most of the ethyl alcohol from the product mixture. The fluid product withdrawn from coils 62 through line 63, in taken to intermediate pressure separator 65 which effects the separation of the alcohol from the noncondensables. The ethyl alcohol product is pumped from separator 65 by pump 66 through line 67, pump 66 serving, if necessary, to finally increase the pressure of the product to atmospheric.

A portion of the product is withdrawn from line 67 through line 68 and throttle valve 69 to be flashed to distillation column pressure into low-pressure reflux separator 70 wherein at least a portion of this product is vaporized to cool the fluid in reflux separator 70 to a temperature essentially to that prevailing in distillation column 10. The cold low-pressure liquid in separator 70 is taken through line 71 as reflux liquid into column 10.

To order to maintain the desired liquid/vapor balance in pump 23, a small amount of product ethyl alcohol from line 68 is also withdrawn through line 72 and throttle valve 73 and if required, noncondensables from line 74, which provides fluid communication between separator 65 and compressor 75, may also be recycled to pump 23 through line 76 and throttle valve 77. As in the case of the embodiments of FIGS. 1-3, the noncondensable purge may be scrubbed with aqueous ethyl alcohol feed in scrubber 34 to remove product ethyl alcohol therefrom.

Although the above detailed description has been presented in terms of separating ethyl alcohol from an aqueous mixture, it will be apparent that it is equally suitable for separating other mixtures of two or more miscible liquid fractions having different boiling points, the liquid fraction having the lower boiling point being handled as the ethyl alcohol product and that having the higher boiling point being handled as the waste water of the example. For each mixture to be separated, the temperature and pressure ranges over which each step may be carried out, as well as the distribution of liquids and vapors to the various steps of the process, will depend upon the properties of the liquid fractions making up the mixtures and the quality of the low-grade heat and cooling liquids available. These operational parameters, which will of course vary from one system to another, may all be readily determined from existing thermodynamic data.

The process of this invention, by using vacuum distillation, makes it possible in some cases to minimize and even eliminate azeotrope formation. Thus in the case of ethyl alcohol water mixtures if the distillation column is operated below 70 torr, no azeotrope is formed. This invention also makes possible the use of low-grade, e.g., waste, heat to operate the reboiler and the employment of the heat pump principle to allow the use of warmer cooling water, or other liquid, than can normally be used. Indeed, the process makes it possible in one embodiment employing additional vapor recompression to provide a system which requires no appreciable external energy save that required to run the pump which must be capable of handling mixtures of liquid and condensing vapor.

It will thus be seen that the objects set forth above, among those made apparent from the preceding description, are efficiently attained and, since certain changes may be made in carrying out the above process and in the constructions set forth without departing from the scope of the invention, it is intended that all matter contained in the above description or shown in the accompanying drawings shall be interpreted as illustrative and not in a limiting sense.

I claim:

1. A process for distillatively separating liquid mixtures containing at least two miscible volatile components having different boiling points, comprising the steps of
   (a) supplying to a distillation column a source of low-grade heat between about 30° C. and about 80° C.;
   (b) supplying a cooling liquid having a temperature up to about 75° C.;
   (c) distilling a liquid mixture of at least two miscible volatile components of different boiling points in said distillation column, to form a lower-boiling fraction and a higher-boiling fraction, under a pressure sufficiently below atmospheric to cause said higher-boiling fraction of said liquid mixture to boil below the temperature of said low-grade heat supplied to said distillation column;
   (d) discharging said higher-boiling fraction from the bottom of said distillation column;
   (e) withdrawing from said distillation column said lower-boiling fraction at a pressure essentially equivalent to that prevailing near the top of said distillation column;
   (f) elevating the pressure of said lower-boiling fraction to a level which is no greater than that which effects the condensing of at least a portion of said lower-boiling fraction above the temperature of said cooling liquid supplied, to form lower-boiling liquid product;
   (g) condensing a portion of said lower-boiling fraction to provide said lower-boiling fraction at a low temperature and at a pressure essentially equal to that prevailing near the top of said distillation column; and
   (h) returning at least a portion of said low-temperature lower-boiling fraction from step (g) to the top of said distillation column as reflux liquid.

2. A process in accordance with claim 1 wherein said step of condensing a portion of said lower-boiling fraction comprises effecting indirect heat exchange between said lower-boiling fraction as it is withdrawn from said distillation column and the cooling liquid to provide said low-temperature liquid lower-boiling fraction.

3. A process in accordance with claim 1 wherein said step of condensing a portion of said lower-boiling fraction includes flashing a portion of said liquid lower-boiling fraction resulting from step (g) to a pressure essentially equal to that prevailing near the top of said distillation column to provide at least a portion of said low-temperature liquid lower-boiling fraction.

4. A process in accordance with claim 3 including the step of effecting indirect heat exchange between said lower-boiling fraction as it is withdrawn from said distillation column and the cooling liquid to provide a portion of said low temperature liquid lower-boiling fraction.

5. A process in accordance with claim 1 including the step of adiabatically compressing said lower-boiling fraction containing said noncondensables withdrawn from said distillation column to elevate the condensing temperature of said mixture; and using the resulting heated mixture as said source of low-grade heat and said higher-boiling fraction as said cooling liquid.

6. A process in accordance with claim 1 wherein said liquid mixture of at least two miscible volatile components contains noncondensables and said process includes the step of separating said noncondensables from said lower-boiling liquid of step (f).

7. A process in accordance with claim 6 including the step of recycling a portion of said noncondensables, subsequent to separation from said lower-boiling liquid as gas ballast in step (f).

8. A process in accordance with claim 6 including the step of compressing said noncondensables, subsequent to separation from said lower-boiling liquid, to essentially atmospheric pressure.

9. A process in accordance with claim 8 including the step of scrubbing said compressed noncondensables with said liquid mixture of at least two miscible volatile components prior to said distilling step.

10. A process for recovering ethyl alcohol from a dilute aqueous mixture containing noncondensable components, comprising the steps of
(a) supplying to a distillation column a source of low-grade heat between about 30° C. and about 80° C.;
(b) supplying a cooling liquid having a temperature up to about 75° C.;
(c) distilling a dilute aqueous mixture of ethyl alcohol and noncondensables in said distillation column, to form an ethyl alcohol product mixture and an aqueous waste mixture, under a pressure sufficiently below atmospheric to cause said aqueous waste mixture to boil below the temperature of said low-grade heat supplied to said distillation column;
(d) discharging said aqueous waste mixture from the bottom of said distillation column;
(e) withdrawing from said distillation column said ethyl alcohol product mixture containing said noncondensables at a pressure essentially equivalent to that prevailing near the top of said distillation column;
(f) elevating the pressure of said withdrawn ethyl alcohol product mixture to a level which is no greater than that which effects the condensing of said ethyl alcohol above the temperature of said cooling liquid supplied, to form ethyl alcohol product and gaseous noncondensables;
(g) separating said liquid ethyl alcohol product and said noncondensables;
(h) throttling a portion of said ethyl alcohol product mixture to provide a low-temperature liquid ethyl alcohol at a pressure essentially equal to that prevailing near the top of said distillation column; and
(i) returning at least a portion of said low-temperature liquid ethyl alcohol from step (h) to the top of said distillation column as reflux liquid.

11. A process in accordance with claim 10 wherein said step of condensing a portion of said ethyl alcohol product mixture comprises effecting indirect heat exchange between said ethyl alcohol product mixture as it is withdrawn from said distillation column and the cooling liquid to provide said low-temperature liquid ethyl alcohol.

12. A process in accordance with claim 10 wherein said step of condensing a portion of said ethyl alcohol product mixture includes flashing a minor amount of said liquid ethyl alcohol product resulting from step (g) to a pressure essentially equal to that prevailing in said distillation column to provide at least a portion of said low-temperature liquid ethyl alcohol.

13. A process in accordance with claim 12 including the step of effecting indirect heat exchange between said ethyl alcohol product mixture as it is withdrawn from said distillation column and the cooling liquid to provide a portion of said low temperature liquid ethyl alcohol.

14. A process in accordance with claim 10 including the step of adiabatically compressing said ethyl alcohol product mixture containing said noncondensables withdrawn from said distillation column to elevate the condensing temperature of said mixture; and using the resulting heated mixture as said source of low-grade heat and said aqueous waste mixture as said cooling liquid.

15. A process in accordance with claim 10 including the step of recycling a portion of said noncondensables, subsequent to their separation in step (g), as gas ballast in step (f).

16. A process in accordance with claim 10 including the step of compressing said noncondensables, subsequent to their separation in step (g), to essentially atmospheric pressure.

17. A process in accordance with claim 16 including the step of scrubbing said compressed noncondensables with said dilute aqueous mixture of ethyl alcohol before distilling thereby to remove residual ethyl alcohol from said noncondensables.

18. A process in accordance with claim 10 wherein said dilute aqueous mixture of ethyl alcohol, insolubles and noncondensables results from the fermentation of one or more agricultural materials.

* * * * *